United States Patent [19]

Pilgram

[11] Patent Number: 4,602,933

[45] Date of Patent: Jul. 29, 1986

[54] PHENYLUREA HERBICIDES

[75] Inventor: Kurt H. Pilgram, Modesto, Calif.

[73] Assignee: Shell Oil Company, Houston, Tex.

[21] Appl. No.: 670,251

[22] Filed: Nov. 13, 1984

[51] Int. Cl.[4] ................... A01N 43/90; C07D 493/08
[52] U.S. Cl. ........................................ 71/88; 549/331; 549/332; 549/334; 549/343; 549/397; 549/463; 549/496
[58] Field of Search ................... 71/88; 549/331, 332, 549/334, 343, 397, 463, 496

[56] References Cited

U.S. PATENT DOCUMENTS 4,166,735  9/1979  Pilgram et al. .................. 71/118

FOREIGN PATENT DOCUMENTS 81893  6/1983  European Pat. Off. .

*Primary Examiner*—Dolph H. Torrence

[57] ABSTRACT

Novel compounds of the formula

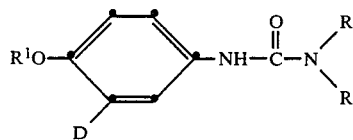

wherein D is hydrogen, halogen, (halo)alkyl or (halo)alkoxy; R is hydrogen, alkyl or alkoxy and $R^1$ is the hydrocarbyl residue of a saturated oxygen-heterocyclic alcohol, are useful as herbicides.

14 Claims, No Drawings

PHENYLUREA HERBICIDES

BACKGROUND OF THE INVENTION

Field of the Invention

The present invention relates to new phenylureas, their use as herbicides and to herbicidal compositions containing these new ureas.

SUMMARY OF THE INVENTION

The present invention is directed to novel compounds of the formula 1

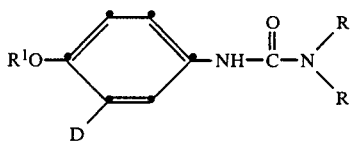

wherein D is a hydrogen atom, a halogen atom of atomic number of from 9 to 35, inclusive, or an alkyl or alkoxy group containing from 1 to 6 carbon atoms optionally substituted by one or more halogen atoms; each R independently is a hydrogen atom or an alkyl or alkoxy group containing from 1 to 4 carbon atoms; and $R^1$ is the residue of a non-aromatic oxygen heterocyclic group having 5 to 8 atoms in a monocyclic or bicyclic ring, one atom of which is an oxygen atom and the remainder are carbon atoms, and containing up to 16 carbon atoms in the group. The compounds are useful as herbicides for controlling (combatting) undesirable or unwanted plants.

The non-aromatic oxygen heterocyclic group, $R^1$, represents the hydrocarbyl portion from known non-aromatic oxygen heterocyclic alcohols. For example, $R^1$ is a group selected from

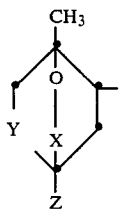

(a)

wherein X is a single bond or —CH(CH$_3$)$_2$—, Y is a single bond or —CH$_2$— with the proviso that both X and Y are not a single bond; and Z is H, or an optionally substituted alkyl group containing 1 to 4 carbon atoms;

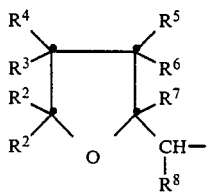

(b)

wherein each $R^2$ individually represents a hydrogen atom, an optionally substituted alkyl, cycloalkyl or aryl group containing up to 6 carbon atoms or two $R^2$ together represent an alkylene moiety each of up to 6 carbon atoms, $R^3$, $R^4$, $R^5$ and $R^6$ each individually represents a hydrogen atom, a halogen atom having an atomic number of from 9 to 35, inclusive, an optionally substituted alkyl, alkoxy, alkylthio or aryl group of up to 6 carbon atoms or one of $R^3$ and $R^4$ and one of $R^5$ and $R^6$ together represent a carbon-carbon bond or an epoxide moiety; $R^7$ and $R^8$ each represents a hydrogen atom or optionally substituted alkyl group of up to 6 carbon atoms;

or

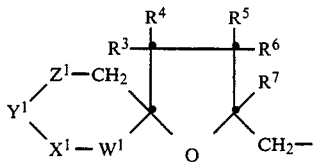

(c)

wherein $R^3$, $R^4$, $R^5$, $R^6$ and $R^7$ each individually is a hydrogen atom or an alkyl group containing from 1 to 4 carbon atoms, W is an oxygen atom or —CH$_2$—; $X^1$ is an oxygen atom or —CH$_2$—; $Y^1$ is a carbon-carbon bond, or an oxygen atom, —CH$_2$—, —C$_2$H$_4$—, or —CHR$^8$— in which $R^8$ is alkoxymethyl group containing from 1 to 4 carbon atoms in the alkyl portion thereof; $Z^1$ is a carbon-carbon bond, an oxygen atom, —CH$_2$—, or —C$_2$H$_4$—; with the proviso that no two adjacent of $W^1$, $X^1$, $Y^1$ and $Z^1$ are simultaneously either oxygen atoms or —C$_2$H$_4$— and the sum of the ring atoms in $W^1$, $X^1$, $Y^1$ and $Z^1$ is an integer of from 2 to 5.

Optional substituents in formulas 1, (a), (b) and (c) include 1 or more atoms of chlorine, fluorine and bromine.

The compounds of formula 1 exhibit geometrical and optical isomerism and can be prepared in geometrical and/or optically-active forms, and as racemates owing to substitution on $R^1$. The various individual optically and geometrical combinations of the materials of the invention usually have some different herbicidal properties. The present invention contemplates all the herbicidally active forms resulting from synthesis and deliberately created mixtures.

The group

can be, for example, a group in which each R independently is hydrogen, methyl, ethyl, propyl or butyl or the corresponding alkoxy groups. Preferably, at least one of R is a methyl group. Because of their herbicidal properties, compounds wherein one R is a methyl group and the other R is a methyl or methoxy group are especially suitable.

The group D can be, for example, hydrogen, chlorine, bromine, fluorine, methyl, ethyl, propyl, trifluoromethyl and the like. Preferred because of their herbicidal properties are those compounds of formula 1 in which D is chlorine, methyl or trifluoromethyl. Especially suitable compounds are those in which D is trifluoromethyl.

The preferred non-aromatic oxygen-heterocycles providing the group $R^1$ include those of formula (a) in which (1) X is a single bond, Y is —CH$_2$— and Z is a hydrogen atom or a 1-methylethyl group or (2) X is —C(CH$_3$)$_2$—, Y is —CH$_2$—, and Z is a hydrogen atom;

preferably X is a single bond, Y is —CH$_2$—, and Z is a 1-methylethyl group; formula (b) in which each R$^2$ independently is a hydrogen atom or a methyl group or the two R$^2$'s taken together from a pentamethylene group, R$^3$, R$^4$, R$^5$, R$^6$ and R$^8$ are hydrogen atoms and R$^7$ is a hydrogen atom, a methyl or ethyl group; preferably each R$^2$ is a methyl group and R$_7$ is a methyl or, especially, an ethyl group; or formula (c) in which W$^1$ is an oxygen atom or —CH$_2$—, X$^1$ is an oxygen atom or —CH$_2$—, Y$^1$ is an oxygen atom, —CH$_2$—, —C$_2$H$_4$— or —CHR$^8$— in which R$^8$ is methoxymethyl, Z$^1$ is an oxygen atom or —CH$_2$—, and the sum of the ring atoms in W$^1$, X$^1$, Y$^1$ and Z$^1$ is an integer of from 3 to 5; preferably, (1) W$^1$ and Z$^1$ are each —CH$_2$— and one of X$^1$ and Y$^1$ is —CH$_2$— and the other is an oxygen atom or (2) W$^1$ is —CH$_2$—, X$^1$ and Z$^1$ each is an oxygen atom and Y$^1$ is —C$_2$H$_4$—.

The compounds of formula 1 of the invention are prepared by converting the appropriately 4-substituted anilines to the corresponding urea product by treatment (a) with alkyl isocyanate, e.g. with heating in a solvent, such as tetrahydrofuran;

(b) with an N,N-dialkylcarbamic chloride or N-alkyl-N-alkoxycarbamoic chloride, e.g. in the presence of a molar equivalent of a tertiary amine hydrogen halide acceptor at elevated temperature; or (c) with phosgene to form the corresponding isocyanate, which is treated with the appropriate amine, NHRR. The reaction with phosgene is conveniently conducted by slowly introducing a solution of the substituted aniline in a solvent, such as ethyl acetate, into a solution of a stoichiometric excess of phosgene in the same solvent, at room temperature, refluxing the mixture and then heating at a higher temperature by gradually allowing some excess phosgene to distill followed by treating the resulting isocyanate with the amine, NHRR.

The precursor 4-substituted anilines are prepared by reducing the correspondingly 4-substituted-nitrobenzene, e.g. by treatment with hydrogen in a Parr shaker at room temperature employing a catalyst, such as Raney nickel or palladium-on-charcoal, and an inert solvent, such as tetrahydrofuran.

The 4-substituted nitrobenzenes are prepared by forming an alkali metal alkoxide of a non-aromatic oxygen-heterocyclic alcohol using, e.g. sodium hydride in an inert solvent, such as dimethyl sulfoxide, and treating the alkoxide with an optionally-3-substituted 4-chloronitrobenzene at room temperature or at moderately elevated temperatures, e.g. of up to about 150° C.

The optionally-3-substituted-4-chloronitrobenzenes are known materials. The non-aromatic oxygen-heterocyclic alcohols are known materials. For example, the alcohols corresponding to residue (a) for formula 1 are known oxabicycloalkanols in European patent No. 81,893 and pending U.S. Ser. No. 416,572 filed Sept. 13, 1982 as a continuation-in-part of U.S. Ser. No. 331,094 filed Dec. 16, 1981, now abandoned. Their preparation is also detailed below. The alcohols corresponding residue (b) for formula 1 are known tetrahydrofurylmethanols described in U.S. Pat. No. 4,116,669. The alcohols corresponding to residue (c) for formula 1 are known oxaspiro derivatives of tetrahydrofurylmethanols described in U.S. Pat. No. 4,410,354.

The oxabicycloalkanol reactants for preparing compounds wherein R$^1$ is a group of formula (a) are obtained generally by one or more of the following routes: directly by (a) epoxidation-cyclization of unsaturated cyclic alcohols, with or without isolation of epoxy alcohol intermediates; and indirectly by (b) Diels-Alder reactions of furans with dienophiles or (c) Birch reduction.

Detailed routes are described below for the different ring systems.

In (a), the epoxidation-cyclization of unsaturated cyclic alcohols involves treatment in an inert solvent with an oxidizing agent followed by an acid. The alcohols are either (i) cycloalk-3-en-1-ols, or (ii) cycloalk-3-ene-1-methanols. The cycloalk-3-en-1-ols are prepared from 1-oxaspiro(2.5)oct-5-enes by hydrogenolysis; from 1-oxaspiro(2.5)-oct-5-enes by rearrangement and partial reduction of the resulting carbonyl compounds; from cycloalk-3-en-1-ones by partial reduction; from cycloalk-3-en-1-ones by treatment with a Grignard reagent; by dealkylating or hydrolyzing, respectively, Diels-Alder adducts of vinyl ethers or esters prepared from dienes, such as isoprene, and vinyl ether or ester dienophiles in which the alpha-position of the vinyl group is substituted by alkyl, CO$_2$R$^8$, or CON(R$^8$)$_2$. The cycloalk-3-ene-1-methanols are (1) alpha-terpineol; (2) Diels-Alder adducts of allylic alcohols; or (3) products obtained from Diels-Alder adducts of alpha-beta unsaturated carbonyl compounds, such as acrylates, crotonates, acrolein or alkyl(methyl)vinyl ketone, by partial reduction or treatment with a Grignard reagent.

In (b), the Diels-Alder type adducts of furans with dienophiles may require vigorous reaction conditions, including high pressure and low temperature, for example, as described in Dauben, W. G. et al., *J. Amer. Chem. Soc.*, 102, page 6894 (1980). When the dienophile is nitroethylene, the resulting product is partially hydrogenated, then oxidized to the ketone and reduced to the corresponding alcohol, e.g. by treatment with a hydride or metal. When this alcohol has the endo form, it can be epimerized with base or aluminum isopropoxide in the presence of a ketone to the corresponding exo alcohol.

Endo- and exo-oxabicycloalkanol intermediates can be separated by conventional methods, such as crystallization, chromatography and the like, and the geometric forms can be resolved by classical resolution methods to give a substantially pure single, optically-active isomer.

Non-limiting illustrations of the preparation of representative Compounds of the Invention follow.

In one embodiment, R$^1$O is derived from an alcohol having the formula I

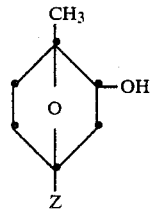

wherein Z has the above meaning. I can be prepared from (1) cyclohex-3-en-1-ols by epoxidation-cyclization, or (2) Diels-Alder adducts of furans, such as 2,5-dimethylfuran, with dienophiles, such as nitroethylene, as described below.

The epoxidation of cyclohex-3-en-1-ols into the corresponding epoxy-alcohol is effected by action of an oxidizing agent, particularly a peroxide, such as m- chloroperbenzoic acid, peracetic acid, tert-butyl hydroperoxide (TBHP) or equivalent peroxide reagents. The oxidation to cis-alcohols with TBHP is conducted in the presence of an appropriate transition metal catalyst, e.g. vanadium. Preferably, the complex is an organic complex, for example, with beta-diketones, o-hydroxybenzaldehydes or o-hydroxybenzophenones and particularly with acetylacetone; for example, vanadium(IV) bis(2,4-pentanedionate) oxide is preferred. The reaction is suitably conducted in the presence of an inert solvent such as chlorinated hydrocarbons, ethers, hydrocarbons or the like. Suitable chlorinated hydrocarbons contain from 1 to 4 chlorine atoms in combination with an alkane chain containing from 1 to 4 carbon atoms or a benzene ring, for example, carbon tetrachloride, chloroform, dichloromethane, chlorobenzene and 1,2- or 1,3-dichlorobenzene and the like. Ethers are generally those containing from 4 to 6 carbon, for example, diethyl ether, methyl tert-butyl ether and diisopropyl ether. Tetrahydrofuran and dioxane are also useful. Suitable alkanes contain from 5 to 10 carbon atoms, for example, n-pentane, n-hexane, n-heptane, n-octane, n-nonane, n-decane and their isomers. Petroleum fractions rich in alkanes are also suitable. Petroleum ether is also suitable. Cyclohexane and methylcyclohexane are examples of useful cycloalkane solvents containing from 6 to 8 carbon atoms. Suitable aromatic hydrocarbon solvents contain from 6 to 10 carbon atoms, for example, benzene, toluene, o-, m-, and p-xylene, the trimethylbenzenes, p-ethyltoluene and the like. The reaction is conducted at temperatures conveniently in the range of from about $-10°$ C. to about $50°$ C. or slightly above. Generally, the temperature is from about $-5°$ C. to about $40°$ C., preferably from about $10°$ C. to about $30°$ C. The molar ratio of reactants can vary. Generally, a molar ratio of cyclohex-3-en-1-ol to oxidizing agent is from about 0.8 to about 1.0. The reaction is usually conducted by forming a mixture of the alcohol and oxidizing agent, preferably while agitating the reaction mixture, e.g. by stirring, and maintaining the desired reaction temperature. The resulting cis-epoxy-alcohol may be purified or converted without isolation into the 2-exo-hydroxy-7-oxabicyclo[2.2.1]-heptane by cyclization as described below.

The cyclization (ring closure) step surprisingly gave a high yield of product having the exo-hydroxy configuration in the resulting 7-oxabicyclo[2.2.1]heptan-2-ol. Many acids will catalyze this reaction, but a relatively strong acid such as sulfuric or sulfonic acids are suitable. Preferably, the acid is methanesulfonic acid or an arylsulfonic acid, such as p-toluenesulfonic, benzenesulfonic acids, or the like. Of these, p-toluenesulfonic acid is preferred. The reaction is suitably conducted by adding the acid to the epoxy-alcohol contained in an inert solvent of the type previously described for use in the preparation of the epoxy-alcohol. The reaction is conducted at a temperature conveniently in the range of from about $0°$ C. to about $50°$ C. or slightly above. Generally, the temperature is from about $5°$ C. to about $40°$ C., preferably from about $10°$ C. to about $30°$ C. The molar ratio of reactants can vary. Generally, the molar ratio of acid to epoxy-alcohol is from about 0.01 to about 0.10, and preferably from about 0.02 to about 0.04.

Thus, a 1,4-disubstituted-3-cyclohexen-1-ol is converted mainly to 2-exo-hydroxy-1,4-disubstituted-7-oxabicyclo[2.2.1]heptane by treating it with an oxidizing agent, such as tert-butyl hydroperoxide, or m-chloroperbenzoic acid, and then a strong acid, such as p-toluenesulfonic acid. Especially useful for obtaining a 2-exo-hydroxy-1,4-disubstituted-7-oxabicyclo[2.2.1]heptane is treatment of the corresponding 3-cyclohexen-1-ol with tert-butyl hydroperoxide and vanadium-(IV) bis(2,4-pentanedionate)oxide as catalyst in methylene chloride followed by treatment of the intermediate epoxide, preferably in situ, with a sulfonic acid, particularly p-toluenesulfonic acid. Also, acid present during the epoxidation step produces the desired product.

The epoxidation-cyclization is disclosed and claimed in copending U.S. patent application Ser. No. 331,095, filed Dec. 16, 1981, and Ser. No. 414,548, filed Sept. 8, 1982, both abandoned and in Ser. No. 559,512, filed Dec. 8, 1983.

In situations where the endo form is desired, it can be obtained by oxidation of the 2-exo-hydroxy compound to the corresponding ketone followed by reduction of the ketone with sodium borohydride.

The 3-cyclohexen-1-ols useful for the preparation of Compound I can also be synthesized as described below or obtained from natural sources (which offer the advantage of optically-active materials).

(a) where Z is 1-methylethyl, the starting compound is terpinen-4-ol, which occurs naturally. Terpinen-4-ol is converted to 2-exo-hydroxy-1-methyl-4-(1-methylethyl)-7-oxabicyclo[2.2.1]heptane by treatment with an oxidizing agent, for example, a peroxide such as m-chloroperbenzoic acid, peracetic acid or tert-butyl hydroperoxide, in an inert solvent in the presence of a strong acid. The spatial configuration of terpinen-4-ol is retained in the reaction product. Thus, ($\pm$), ($-$) or ($+$) 2-exo-hydroxy-1-methyl-4-(1-methylethyl)-7-oxabicyclo[2.2.1]heptane can be obtained. 2-endo-Hydroxy-1-methyl-4-(1-methylethyl)-7-oxabicyclo[2.2.1]heptane is known from Garside et al., *J. Chem. Soc.*, page 716–721 (1969). 2-exo- and endo-Hydroxy-1-methyl-4-(1-methylethyl)-7-oxabicyclo[2.2.1]heptanes are converted to the ethers of the invention as described above. Although terpinen-4-ol occurs in nature in optically active and racemic forms, it can also be prepared by epoxidation of terpinolene, e.g. with peracetic acid in methylene chloride, followed by reduction of the epoxide, e.g. with sodium diethylaluminum hydride in tetrahydrofuran.

(b) Preparation of 3-cyclohexen-1-ols can be effected from p-substituted phenols in which the substituent group corresponds to methyl in the formula I of the invention by procedures of the literature for the Birch-type reduction of derivatives of benzene, many of which are detailed in Rodd's Chemistry of Carbon Compounds, Second Edition, *Vol. II, Part B*, pages 1–4 (1968). In an example, para-cresol is first methylated to protect the hydroxy group yielding the corresponding p-methylanisole. This p-methylanisole is treated with a reducing agent such as lithium-ammonia or sodium-ammonia and the resulting product is hydrolyzed to yield the corresponding 4-methyl-3-cyclohexen-1-one. Treatment of this ketone with an appropriate organometallic (Grignard) reagent, ZMgBr or ZLi in which Z corresponds to that in the formula I of the invention and is alkyl, e.g. at $20°$–$60°$ C. in the presence of anhydrous ethers, yields the desired 1,4-disubstituted-3-cyclohexen-1-ol intermediate. The 4-methyl-3-cyclohexen-1-one can also be reduced, e.g. by hydrides, to the corresponding 3-cyclohexen-1-ol unsubstituted in position-1.

The 2-hydroxy-7-oxabicyclo[2.2.1]heptanes useful as precursors of compounds of the invention can also be prepared from Diels-Alder adducts of suitably-substituted furans, as dienes, and dienophiles. For example, 2,5-dimethylfuran adds readily to nitroethylene to give 1,4-dimethyl-2-nitrobicyclo[2.2.1]hept-5-ene. Similar adducts can be prepared from 2,5-dialkylfurans and dienophiles such as acrolein and acrylate esters.

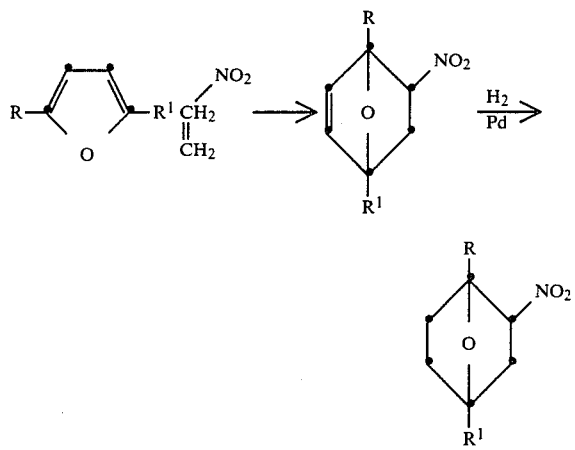

Severe reaction conditions including low temperature and high pressure may be required for some Diels-Alder reactions of substituted furans, for example, as described in Dauben, W. G. et al., *J. Am. Chem. Soc.*, 102, page 6894 (1980). Hydrogenation and treatment of the nitro compound with a strong base such as potassium hydroxide, followed by an oxidizing agent, such as potassium permanganate, singlet oxygen, aqueous $TiCl_3$, tert-butyl hydroperoxide in the presence of vanadium(IV) bis(2,4-pentanedionate)oxide or the like, affords the 1,4-disubstituted bicyclo[2.2.1]heptan-2-one. Reduction with a hydride or metal converts the ketone to the desired 2-hydroxybicyclo[2.2.1]heptane useful for preparation of compounds of the invention by aralkylation. Where the hydroxy group is in the endo orientation, epimerization to the more desirable 2-exo-hydroxy stereoisomer can be effected by treatment with a base, such as sodium hydroxide, or aluminum alkoxide in the presence of a ketone, preferably the corresponding ketone.

In another embodiment of the invention, $R^1O$ is derived from an alcohol having the formula II

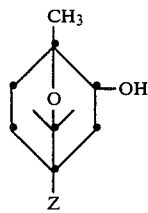

wherein Z has the above meaning. II (2-oxabicyclo[2.2.2]heptan-6-ols) can be prepared from (1) terpenes, such as alpha-terpineol, or (2) Diels-Alder adducts of suitably substituted butadienes and dienophiles containing an oxygen function, as illustrated below. For example, (1) the compound is obtained from naturally occuring terpenes. Most elementarily, alpha-pinene is treated with aqueous acid to form alphaterpineol, itself a naturally occuring material. alpha-Terpineol, either in racemic form or completely or partially optically active form, is oxidized, for example, with a peroxide such as hydrogen peroxide or m-chloroperbenzoic acid in a suitable solvent like methylene chloride, to yield a major amount of 1,3,3-trimethyl-2-oxabicyclo[2.2.2]octan-6-exo-ol (hydroxy group anti to oxygen-containing bridge). Oxidation of this alcohol, e.g. with N-bromoacetamide in aqueous acetone at 5° C., gives 1,3,3-trimethyl-2-oxabicyclo[2.2.2]octan-6-one. Subsequent reduction of this ketone, for example with sodium borohydride in tert-butanol, yields a mixture of alcohols predominant in the endo isomer (hydroxy group syn to oxygen-containing bridge). Conversion to the ether of formula 1 of the Invention follows the earlier described procedures with retention of configuration.

(2) Diels-Alder adducts are formed from suitable, readily available dienophiles including an acrylate ester, acrolein, methacrolein, methyl vinyl ketone, allyl alcohol, a crotonate ester and the like. The diene component is isoprene, 2,3-dimethylbutadiene and the like. For example, the Diels-Alder adducts IIa are prepared by treating the portion of the compound of formula IIa above the dotted line

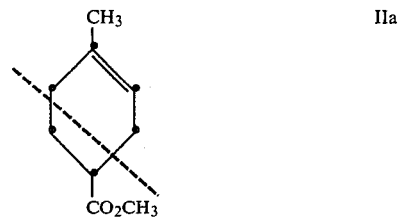

with a dienophile (methyl acrylate) corresponding to the portion of the compound of formula IIa below the dotted line. Many such reactions are detailed in Rodd's Chemistry of Carbon Compounds, Second Edition, Vol II, Part B, pages 5–6 (1968). Treatment of IIa with the appropriate Grignard reagent (e.g. methyl magnesium bromide, ethyl magnesium bromide or the like) gives an alpha,alpha,4-trimethyl-cyclohexene-1-methanol of formula IIb below.

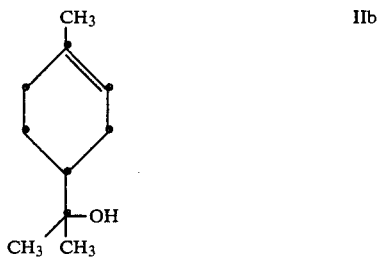

Alcohol IIb is oxidized, for example, with a peroxide, such as hydrogen peroxide or m-chloroperbenzoic acid, in a suitable solvent, such as methylene chloride, preferably in the presence of a strong acid, to yield a major amount of 1,3,3-trimethyl-2-oxabicyclo[2.2.2]octan-6-exo-ol. This exo form can be converted, if desired, into an endo-rich or substantially pure endo form. First, oxidation to the corresponding ketone, 1,3,3-trimethyl-2-oxabicyclo[2.2.2]octan-6-one, is effected with a suitable oxidizing agent. For example, the exo form is combined with oxalyl chloride and dimethyl sulfoxide in methylene chloride followed by addition of triethylamine. Then, the resulting ketone is converted into the endo-alcohol by reduction. For example, the ketone in a mixture of dimethoxyethane and tert-butanol is treated with sodium borohydride. Classical resolution can be applied to the 1,3,3-trialkyl-2-oxabicyclo[2.2.2]octan-6-ols to give substantially pure individual optical forms. The 1,3,3-trialkyl-2-oxabicyclo[2.2.2]octan-6-ols are converted into the desired ethers of the Invention, with retention of configuration. This reaction is carried out, preferably in the presence of a base, such as sodium hydride, and, if desired, an inert solvent, such as N,N-dimethylacetamide, N,N-dimethylformamide, benzene, toluene or the like. The compounds of the invention can be recovered and purified by conventional techniques.

In another embodiment of the invention, $R^1O$ is derived from an alcohol having the formula III

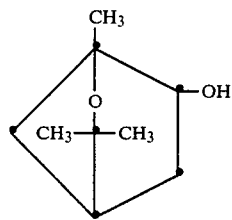

III

III can be prepared by condensation of 1,4-dibromo-2-methyl-2-butene with an alkyl acetoacetate, in the presence of base, followed by thermolysis of the 2-isopropenyl-1-acetylcyclopropanecarboxylate intermediate to a 1-acetyl-3-methyl-3-cyclopentenecarboxylate, which is hydrolyzed and decarboxylated to the corresponding ketone. Treatment of the ketone with two equivalents of Grignard reagent, methyl magnesium bromide, yields the corresponding alcohol derivative. This alcohol is epoxidized and cyclized to 1,3,3-trimethyl-2-oxabicyclo[2.2.1]heptan-exo-6-ol (III). This exo-alcohol can be oxidized to the corresponding ketone followed by reduction to a corresponding endo-2-oxabicyclo[2.2.1]-heptan-6-ol as described for the compounds of formula II above. An example of one alternative method is the condensation of a 1,4-dibromo-2-methyl-2-butene with a malonic acid dialkyl ester, again using base, followed by thermolysis. The resulting cyclopentene derivative is treated with, e.g., sodium chloride in dimethyl sulfoxide to eliminate one of the ester functional groups. Treatment of the resulting mono ester with the Grignard reagent, methyl magnesium bromide, yields the alcohol derivative described in the first methodology. See, also, Spurlock et al., *Chemical Abstracts,* 76:153024e (1972) for preparation of a 2-oxabicyclo[2.2.1]heptan-6-ol.

ILLUSTRATIVE EMBODIMENTS

The invention is illustrated by the following embodiments which describe the preparation of typical species of the invention. The embodiments are presented for the purpose of illustration only, and should not be regarded as limiting the invention in any way. The identity of the products, including intermediates, was confirmed by elemental, infrared and nuclear magnetic resonance spectral (NMR) analyses as necessary.

EMBODIMENT 1

(±)-2-exo-Hydroxy-1-methyl-4-(1-methylethyl)-7-oxabicyclo[2.2.1]heptane

To a solution of 22.3 g of 85% m-chloroperbenzoic acid in 150 ml of methylene chloride was added over 40 minutes a solution of 15.4 g of (±)-terpinen-4-ol in 30 ml methylene chloride at a temperature of about 0° C. The reaction mixture was stirred for 20 hours at room temperature, then cooled to 5° C. A solid was filtered and rinsed with cold methylene chloride. The combined filtrates were washed successively with one-eighth saturated potassium carbonate, saturated sodium sulfite, and then water, dried and Claisen distilled to yield 8.9 of product, b.p. 109°–113° C. at 8 mm. Recrystallization of the solidified distillate from pentane gave 5.5 g of the desired product, m.p. 42°–58° C.

EMBODIMENT 2

(±)-2-exo-Hydroxy-1-methyl-4-(1-methylethyl)-7-oxabicyclo[2.2.1]heptane

To a solution of 30.8 g of (±)-terpinen-4-ol and 0.8 g of vanadium(IV) bis(2,4-pentanedionate)oxide in 300 ml of methylene chloride was added 22.0 g of 90% tert-butyl hydroperoxide. The resulting reaction, initially mildly exothermic, was held at reflux for 2 hours, to obtain the epoxide, then 0.8 g of p-toluenesulfonic acid in 10 ml of glyme was added. The resulting reaction mixture was refluxed for 1.5 hours, and cooled, and 0.8 g of anhydrous sodium acetate was added with stirring. After filtration, the filtrate was concentrated and Claisen distilled to give 28.4 g of the desired product, b.p. 80°–95° (2 mm).

EMBODIMENT 3

Benzene, 1-chloro-2-[(±)-1-methyl-4-(1-methylethyl)-7-oxabicyclo[2.2.1]hept-2-exo-yloxy]-5-nitro- To a solution of 84.5 g of the alcohol of Embodiment 2 above, in 1,000 ml of dimethyl sulfoxide was added portionwise with stirring 12.0 g of sodium hydride. The mixture was stirred at room temperature for 45 minutes, then heated at 60° C. for 1 hour. After the mixture had cooled to 25° C., 96 g of 3,4-dichloronitrobenzene was added dropwise, followed by heating of the resulting mixture to 60° C. (1 hour). The mixture was drowned in ice water and extracted with methylene chloride. The extract was washed with water, dried (MgSO₄), and concentrated under rotary evaporation. The residual oil was purified by silica chromatography using the solvent mixture (by volume) tetrahydrofuran (4), ethyl acetate (16), hexane (80), as eluent. The major fraction was 45.6 g of the desired product, as a yellow crystalline solid, m.p. 94° C.

EMBODIMENT 4

Benzeneamine, 3-chloro-4-[(±)-1-methyl-4-(1-methylethyl)-7-oxabicyclo[2.2.1]hept-2-exo-yloxy]-

A solution containing 45.6 g of the nitro compound of Embodiment 3 above in 800 ml of tetrahydrofuran was hydrogenated in a Parr shaker over 5% palladium-on-charcoal catalyst at 35 psi hydrogen pressure. Filtration followed by rotary evaporation gave the desired product in quantitative yield as a yellow viscous oil, which was used without further purification in the following reactions.

EMBODIMENT 5

Urea,
N-methyl-N'-[3-chloro-4-[(±)-[1-methyl-4-(1-methylethyl)-7-oxabicyclo[2.2.1]hept-2-exo-yloxy]phenyl]-

To a solution of 5.0 g the aniline of Embodiment 4 above, and 5 drops of triethylamine in 75 ml of ether was added 1.14 g of methyl isocyanate. This addition was exothermic to 27° C. After 0.5 hour, the reaction mixture was concentrated under rotary evaporation. The residue was crystallized from ether-hexane to give 6.0 g of the desired product as a white solid; m.p. 180°–181° C.

EMBODIMENT 6

Isocyanic acid,
3-chloro-4-[(±)-1-methyl-4-(1-methylethyl)-7-oxabicyclo[2.2.1]hept-2-exo-yloxy]phenyl ester Into a cooled (5°–10° C.) and stirred solution of 26.6 g of the aniline of Embodiment 4 in 250 ml of ethyl acetate was introduced through a gas-inlet tube 5.1 g of hydrogen chloride followed by 17.8 g of phosgene. The mixture was stirred and refluxed (Dry Ice-acetone condenser) for 4 hours, and concentrated under rotary evaporation to give 28.9 g of the desired product as a yellowish solid.

EMBODIMENT 7

Urea,
N,N-dimethyl-N'-[3-chloro-4-[(±)-1-methyl-4-(1-methylethyl)-7-oxabicyclo[2.2.1]hept-2-exo-yloxy]-phenyl]-

Dimethylamine, 2.0 g, was introduced with the aid of a gas-inlet tube into a stirred solution of 14.5 g of the isocyanate of Embodiment 6 above in 150 ml of tetrahydrofuran. This addition was exothermic. The mixture was refluxed for 2 hours and concentrated under rotary evaporation. The residue was washed well with cold ether and dried to give 14.3 g of the desired product as a off-white solid; m.p. 154°–155° C.

EMBODIMENT 8

Urea,
N-methoxy-N-methyl-N'-[3-chloro-4-[(±)-1-methyl-4-(1-methylethyl)-7-oxabicyclo[2.2.1]hept-2-exo-yloxy]-phenyl- To a stirred solution of 14.5 g of the substituted phenylisocyanate of Embodiment 6 above in 100 ml of tetrahydrofuran was added 2.75 g of O,N-dimethylhydroxylamine. The mixture was heated to 56° C. for 2 hours, concentrated under reduced pressure and recrystallized from ether-hexane, to give 11.3 g of the desired product as a white solid; m.p. 110°–112° C.

EMBODIMENT 9

Toluene,
2-[(±)-1-methyl-4-(1-methylethyl)-7-oxabicyclo[2.2.1]hept-2-exo-yloxy]-5-nitro-α,α,α-trifluoro- To a stirred solution of 18.1 g of the alcohol of Embodiment 2 above in 200 ml of dimethyl sulfoxide was added portionwise 2.64 g of sodium hydride. After 1 hr at room temperature, the mixture was heated to 60° C. for 0.5 hours. To the cooled reaction mixture containing the sodium alcoholate was added dropwise 24.8 g of 2-chloro-5-nitrobenzotrifluoride. This addition was exothermic to 60° C. The reaction mixture was heated at 60° C. for 0.5 hours, drowned in ice water and extracted repeatedly with methylene chloride. The combined extracts were washed with water, dried (anhydrous MgSO4), filtered and concentrated. The residual oil was purified by silica chromatography using the solvent mixture (by volume) tetrahydrofuran (4), ethyl acetate (16), hexane (80), as eluent.

The first fraction consisted of 13.0 g of the desired product as a yellow crystalline solid; m.p. 95° C.

A second fraction consisted of 0.5 g of an isomer of the desired product derived from 4-chloro-5-nitrobenzotrifluoride present in the purchased starting material; m.p. 94° C., a white crystalline solid.

EMBODIMENT 10

Benzeneamine,
4-[(±)-1-methyl-4-(1-methylethyl)-7-oxabicyclo[2.2.1]hept-2-exo-yloxy]-3-(trifluoromethyl)-

A solution of 13.0 g of the nitro compound of Embodiment 9 above in 200 ml of tetrahydrofuran was hydrogenated over 5% palladium-on-charcoal catalyst (0.5 g) and a hydrogen pressure of 40 lbs. After 5 hours in the Parr shaker, the reaction mixture was filtered and concentrated under rotary evaporation to give 11.8 g of the desired amine as a yellow viscous liquid which was used in the next reaction step without further purification.

EMBODIMENT 11

Urea,
N-methyl-N'-[4-[(±)-1-methyl-4-(1-methylethyl)-7-oxabicyclo[2.2.1]hept-2-exo-yloxy]-3-(trifluoromethyl)-phenyl]

A solution containing 5.2 g of the amine of Embodiment 10 above and 1.8 g of methyl isocyanate in 100 ml of ether containing 3 drops of triethylamine was left standing at room temperature for 2 days. The solvent was removed by rotary evaporation. Crystallization from ether-hexane of the residue gave 4.8 g of off-white solid;
m.p. 173°–175° C.

EMBODIMENT 12

Urea,
N-methoxy-N-methyl-N'-[4-[(±)-1-methyl-4-(1-methylethyl)-7-oxabicyclo[2.2.1]hept-2-exo-yloxy]-3-(trifluoromethyl)phenyl]-

To a stirred solution of 5.2 g of the amine of Embodiment 10 above in 175 ml of pyridine was added dropwise 4.0 g of N-methoxy-N-methylcarbamic chloride. After standing overnight at room temperature, the reaction mixture was drowned in ice water, acidified with hydrochloric acid, and extracted with methylene chloride. The extracts were dried and concentrated under rotary evaporation to give 5.5 g of the desired product as an amber syrup which did not crystallize.

EMBODIMENT 13

Isocyanic acid,
3-(trifluoromethyl)-4-[(±)-1-methyl-4-(1-methylethyl)-7-oxabicyclo[2.2.1]hept-2-exo-yloxy]phenyl ester.

This isocyanate was prepared from the aniline of Embodiment 10 above following the procedure described for the analogous chlorosubstituted phenyl isocyanate. The crude isocyanate was used without purification in the next reactions.

EMBODIMENT 14

Urea,
N,N-dimethyl-N'-[4-[(±)-1-methyl-4-(1-methylethyl)-7-oxabicyclo[2.2.1]hept-2-exo-yloxy]-3-(trifluoromethyl)phenyl]-

To a stirred solution of 5.3 g of the isocyanate of Embodiment 13 above, in 75 ml of tetrahydrofuran, was added through a gas-inlet tube 0.8 g of dimethylamine. After 24 hours, the solvent was removed by rotary evaporation. The residue was purified by silica chromatography using the solvent mixture (by volume), tetrahydrofuran (4), ethyl acetate (30), hexane (66).

The first fraction consisted of 1.7 g tan solid; m.p. 103°–104° C.; ir (KBr) 3400 (—OH, NH), 3000-2800 (—CH), 1736 (C=O)(ester), 1651 (C=O,amide), 1503 (CONH), 1325 (CF$_3$), 1254-1053 cm$^{-1}$(C—OC); li/ms m/z 478 (M+), 443 (M+—Cl),

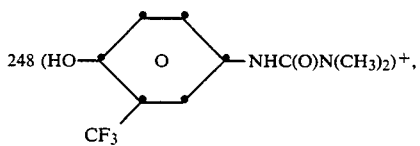

72 ((CH$_3$)$_2$NCO+), 43 (C$_3$ Mg+);

Anal found: C, 52.7 H, 6.0 N, 5.4
The structure of this fraction is unknown.
The second fraction was 1.2 g of the desired product as a brown oil.
The third fraction was identified as N,N-dimethyl-N'-(hydroxy-3-(trifluoromethyl)phenyl)urea; yield, 0.4 g; m.p. 217° C. as a white solid.

EMBODIMENT 15

Urea,
N-methyl-N'-[4-[(±)-1-methyl-4-(1-methylethyl)-7-oxabicyclo[2.2.1]hept-2-exo-yloxy]-phenyl]-

Following procedures similar to those described in Embodiments 9–11 above, the desired product was obtained by treating the alcohol of Embodiment 2 above with 4-chloronitrobenzene, reducing the nitro group to an amine and treating the amine is treated with methyl isocyanate.

EMBODIMENT 16

Urea,
N,N-dimethyl-N'-[4-[(±)-1-methyl-4-1-(methyl-ethyl)-7-oxabicyclo[2.2.1]hept-2-exo-yloxy]phenyl]-

Following procedures similar to those described in Embodiments 9, 10, 13 and 14 above, the desired product was prepared by treating the alcohol of Embodiment 2 above with 4-chlorobenzene, reducing the nitro group to an amine, followed by conversion to the isocyanate and then the N,N-dimethylurea product.

EMBODIMENT 17

Urea,
N-methyl-N-methoxy-N'-[4-[(±)-1-methyl-4-(1-methylethyl)-7-oxabicyclo[2.2.1]hept-2-exo-yloxy]-phenyl]-

Following procedures similar to those described in Embodiments 9, 10 and 12 above, the desired product was prepared by treating the alcohol of Embodiment 2 above with 4-chloronitrobenzene, reducing the nitro group to an amine followed by conversion to the 1-methyl-1-methoxyurea with N-methyl-N-methoxycarbamic chloride.

EMBODIMENT 18

1,7-Dioxaspiro[4.5]decane,
2-ethyl-2-(4-nitro-2-trifluoromethyl)phenoxymethyl)-

To a solution stirred under nitrogen at room temperature of 30 g of 2-ethyl-2-(hydroxymethyl)-1,7-dioxaspiro[4.5]decane in 300 ml of dimethyl sulfoxide was added in small portions 7.9 g 50% sodium hydride-mineral oil dispersion, which has been washed with hexane. After evolution of gas ceased, the solution was warmed briefly to 40° C., then cooled to room temperature. To it was added dropwise 22.1 ml of 2-chloro-5-nitrobenzotrifluoride at such a rate that the temperature stayed below 40° C. After the addition was complete, the suspension was stirred at room temperature for 2 hours, then poured into 2 liters of weakly acidic ice water. A light brown tar separated, which was dissolved in ether. This solution was washed with water, dried (MgSO$_4$), and concentrated to give 50 g of the desired product as an amber oil.

EMBODIMENT 19

1,7-Dioxaspiro[4.5]decane,
2-ethyl-2-(4-amino-2-(trifluoromethyl)phenoxymethyl)-

A 2 liter Parr hydrogenation bomb was charged with a solution of 48 g of the nitro compound of Embodiment 18 above in 500 ml of tetrahydrofuran and 3 g of 10% Pd on charcoal. This was shaken under 35 psi hydrogen for 18 hours. It was then filtered through MgSO$_4$ and reacted without further isolation.

EMBODIMENT 20

Urea,
N-methoxy-N-methyl-N'-(3-trifluoromethyl)-4-(2-ethyl-1,7-dioxaspiro[4.5]dec-2-ylmethoxy)phenyl)-

To a solution stirred at room temperature of 12 g of the aniline of Embodiment 19 in 130 ml of tetrahydrofuran was added dropwise 5.0 g methoxy methyl carbamic chloride, and 4.6 ml of triethyl amine. The solution was allowed to stir at room temperature for 18 hours. It was then concentrated, diluted with ether, and extracted with 10% aqueous HCl. The organic phase was dried (MgSO$_4$), concentrated, and chromatographed on silica gel (tetrahydrofuran:ethyl acetate:-hexane, 4:30:66) to yield a total of 12 g of a viscous yellow oil; containing 1.5 g each of the two pure diastereomers, (A) cis and (B) trans and 9 g of (C), a mixture of the two isomers.

EMBODIMENT 21

Urea,
N-methyl-N'-(3-(trifluoromethyl)-4-(2-ethyl-1,7-dioxaspiro[4.5]dec-2-ylmethoxy)phenyl)-

To a solution stirred at room temperature of 12.0 g of the aniline of Embodiment 19 in 130 ml of tetrahydrofuran was added dropwise 2.4 ml methyl isocyanate followed by 5 drops triethyl amine. The solution was stirred at room temperature for 18 hours, concentrated, and crystallized from hexane/ether to yield 4.6 g of (A) the trans isomer as white needles, m.p. 155°–8° C.; concentration of the mother liquor gave 7.6 g of (B) the cis isomer as a brown oil, containing 20% isomer (A).

EMBODIMENT 22

1-oxaspiro[4.5]decane,
2-ethyl-2-(4-nitro-2-(trifluoromethyl)phenoxymethyl)-

To a solution stirred under nitrogen at room temperature of 30 g of 2-ethyl-2-(hydroxymethyl)-1-oxaspiro[4.5]decane in 300 ml of dimethyl sulfoxide was added in small portions 8.0 g 50% sodium hydride-mineral oil dispersion, which has been washed with hexane. After evolution of gas ceased, the solution was warmed briefly to 40° C., then cooled to room temperature. To this was added dropwise 34.0 g 2-chloro-5-nitrobenzotrifluoride at such a rate that the temperature stayed below 40° C. The solution was heated to 60° C. for 1 hour, then cooled to room temperature and poured into 2 liters of ice water. This suspension was extracted with three 500 ml portions of ether. The combined organic extracts were dried (MgSO$_4$), treated with charcoal, and diluted with hexane to yield 29.6 g of the desired product as a yellow solid; m.p. 75°–78° C.

EMBODIMENT 23

1-oxaspiro[4.5]decane,
2-ethyl-2-(4-amino-2-(trifluoromethyl)phenoxymethyl)-

A 500 ml Parr hydrogenation bomb was charged with a solution of 27.3 g of the nitro compound of Embodiment 22 above in 250 ml of tetrahydrofuran and 2 g of 10% Pd on charcoal. This was then shaken under 48 psi of hydrogen for 18 hours. The suspension was then filtered through MgSO$_4$ and reacted without further isolation.

EMBODIMENT 24

Urea,
N-methoxy-N-methyl-N'-(3-(trifluoromethyl)-4-(2-ethyl-1-oxaspiro[4.5]dec-2-ylmethoxy)phenyl)-

To a solution stirred at room temperature of 6.0 g of the aniline of Embodiment 23 in 70 ml of tetrahydrofuran was added dropwise 2.5 g methoxy methyl carbamic chloride, followed by 2.4 ml of triethyl amine. The solution was allowed to stir for 2 hours, then diluted with 80 ml of ether and extracted with 5% aqueous HCl. The organic phase was dried and concentrated to yield 7.0 g of the desired product as an amber oil.

EMBODIMENT 25

Urea,
N-methyl-N'(3-trifluoromethyl)-4-(2-ethyl-1-oxaspiro[4.5]dec-ylmethoxy)phenyl- Following procedures similar to those described in Embodiment 14 above, the desired product was prepared from the anilide of Embodiment 23 above.

EMBODIMENT 26

1-oxaspiro[4.5]decane,
2-ethyl-2-(2-chloro-4-nitrophenoxymethyl)-

To a solution stirred under nitrogen at room temperature of 10 g of 2-ethyl-2-(hydroxymethyl)-1-oxaspiro[4.5]decane in 300 ml of dimethyl sulfoxide was added in small portions 2.7 g 50% sodium hydride—mineral oil. After evolution of gas ceased, the solution was warmed briefly to 40° C., then allowed to cool to room temperature. A solution of 9.7 g 3,4-dichloronitrobenze in 65 ml of dimethylsulfoxide was then added dropwise at such a rate that the temperature did not exceed 40° C. After the addition was complete the solution was allowed to stir at room temperature for 1 hour. It was then poured into 2 l of weakly acidic ice water, which was subsequently extracted with three 500 ml portions of ether. The combined organic extracts were dried (MgSO$_4$), concentrated, and chromatographed on silica gel (CH$_2$Cl$_2$) to yield 13 g of the desired product as an amber oil.

EMBODIMENT 27

1-oxaspiro[4.5]decane,
2-ethyl-2-(4-amino-2-chlorophenoxymethyl)-

A 500 ml Parr hydrognation bomb was charged with a solution of 10.5 g of the nitro compound of Embodiment 26 above in 200 ml of tetrahydrofuran and 1.0 g 10% palladium on charcoal. This suspension was shaken under 43 psi of hydrogen for 18 hours. It was then filtered through MgSO$_4$ and the solution was reacted without further isolation.

EMBODIMENT 28

Urea,
N-cyclopropyl-N'-(3-chloro-4-(2-ethyl-1-oxaspiro[4.5]-dec-2-ylmethoxy)phenyl)-

A 500 ml flask equipped with mechanical stirrer and dry-ice condenser was charged with 100 ml of 12.5% phosgene in benzene (ca. 10 fold excess). To this was added dropwise a solution of 4.5 g of the aniline of Embodiment 27 above in 45 ml toluene. After the addition was complete the solution was heated to 40° C. for 3 hours. It was then concentrated, diluted with 100 ml of ether, and 1.2 ml of cyclopropyl amine was added dropwise. It was allowed to stir at room temperature for 15 minutes, then concentrated to yield 5.5 g of the desired product as an amber oil.

For application, the compound of Formula 1 ordinarily is applied most effectively by formulating it with a suitable inert carrier or surface-active agent, or both. The invention, therefore, also includes compositions suitable for combatting unwanted plants, such compositions comprising an inert carrier or surface-active agent, or both, and as active ingredient at least one compound of Formula 1.

The term "carrier" as used herein means an inert solid or liquid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides, are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonities and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25 to 75% by weight of active compound and usually contain, in addition to the solid carrier, 3–10% by weight of a dispersing agent, 2–15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Of particular interest in current practice are water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or (up to 95%) more by weight of finely divided active material, 3–7% by weight of a blend of surfactants, which act as wetting, dispersing, suspending and binding agents, and may contain up to 3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

It is evident from the foregoing that this invention contemplates compositions containing as little as about 0.5% by weight to as much as about 95% by weight of a compound of Formula 1 as the active ingredient.

The compositions of the invention may also contain other ingredients, for example, other compounds possessing pesticidal, especially insecticidal, acaricidal, herbicidal or fungicidal properties, as are appropriate to the intended purpose.

Protection of a locus or area from undesirable plants is effected by applying a compound of Formula 1, ordinarily in a composition of one of the aforementioned types, to soil in which the seeds of the unwanted plants are present, or to the foliage of the unwanted plants. The active compound, of course, is applied in an amount sufficient to exert the desired action.

The amount of the compound of the invention to be used in combatting undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.1 to 10.0 kg per hectare of the compound of Formula 1 will be satisfactory.

EXAMPLES OF ACTIVITY WITH RESPECT TO PLANTS

In the following examples, the species of plants that were tested were:
Barnyardgrass (watergrass)-*Echinochloa crus-galli*
Large crabgrass-*Digitaria sanguinalis*
Downy brome-*Bromus tectorum*
Yellow foxtail-*Setaria lutescens*
Redroot pigweed-*Amaranthus retroflexus*
Sicklepod-*Cassia obtusifolia*
Velvetleaf-*Abutilon theophrasti*
Garden cress-*Lepidium sativum*
Johnson grass-*Sorghum halepense*
Morningglory-*Ipomoea* sp.

TEST PROCEDURES

The preemergence (soil) herbicidal activity of compounds of Formula 1 was evaluated by planting seeds of barnyardgrass, garden cress, downy brome, velvetleaf, yellow foxtail, and sicklepod in test tubes, nominally measuring 25×200 millimeters, filled about three-quarters full of untreated soil, in each case covered on top with about 2.5 cubic centimeters of soil treated with a certain amount of the test compound. The treated soil applied to the tubes containing the barnyardgrass and cress seeds contained one milligram of the test compound per tube, and contained 0.1 milligram of the test compound per each tube containing the seeds of the other plants. The dosages were approximately 20 and 2.0 pounds of test compound per acre, respectively. The seeds were planted on top of the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
| --- | --- |
| 9 | No living tissue |
| 8 | Plant severely damaged and expected to die |
| 7 | Plant badly damaged, but expected to live |
| 6 | Moderate damage, but complete recovery expected |
| 5 | Intermediate damage (probably unacceptable for crop plants) |
| 3-4 | Observable damage |
| 1-2 | Plant slightly affected, possibly by the chemical, possibly due to biological variability |
| 0 | No visible effect |

The postemergence (foliar) herbicidal activity of compounds of Formula 1 was evaluated by spraying 10-day-old large crabgrass plants, 13-day-old pigweed plants, 6-day-old johnson grass plants, 9-day-old velvetleaf plants, 9-day-old yellow foxtail plants and either 9-day-old sicklepod plants or 5-day-old morningglory plants to runoff with a liquid formulation of the test compound. The crabgrass and pigweed plants were sprayed with 2.4 milliliters of a 0.25% solution (about ten pounds of the test compound per acre), and other plants were sprayed with 2.4 milliliters of a 0.025% solution (about one pound of the test compound per acre). The sprayed plants were held under controlled conditions of temperature, moisture and light for 7 to 8 days, when the effect of the test compound was evaluated visually, the results being rated on the 0 to 9 scale described above.

Results of the preemergence and postemergence herbicidal activity tests are set forth in Table I.

TABLE I

| | HERBICIDAL ACTIVITY | | | | | | | | | | | |
| --- | --- | --- | --- | --- | --- | --- | --- | --- | --- | --- | --- | --- |
| | Preemergence | | | | | | Postemergence | | | | | |
| Compound | Barnyard-grass | Garden Cress | Downy Brome | Velvet-leaf | Yellow Foxtail | Morning-glory | Crab-grass | Pig-weed | Johnson-grass | Velvet-leaf | Yellow Foxtail | Morning-glory |
| 15 | 6 | 9 | 0 | 7 | 2 | 2 | 4 | 6 | 0 | 5 | 0 | 2 |
| 5 | 5 | 9 | 0 | 6 | 2 | 2 | 9 | 9 | 7 | 7 | 8 | 8 |
| 7 | 8 | 9 | 2 | 5 | 2 | 8 | 7 | 9 | 5 | 7 | 7 | 8 |
| 8 | 8 | 9 | 0 | 5 | 0 | 3 | 9 | 9 | 2 | 7 | 8 | 8 |
| 14 | 5 | 5 | 2 | — | 2 | 3 | 9 | 9 | 7 | 7 | 9 | 6 |
| 16 | 7 | 9 | 2 | 5 | 4 | 2 | 2 | 6 | 1 | 4 | 0 | 3 |
| 17 | 7 | 9 | 2 | 6 | 4 | 3 | 2 | 6 | 1 | 5 | 0 | 7 |
| 11 | 5 | 9 | 0 | 3 | 0 | 3 | 7 | 9 | 7 | 8 | 9 | 8 |
| 12 | 4 | 9 | 0 | 3 | 0 | 3 | 6 | 9 | 7 | 2 | 9 | 8 |
| 21B | 0 | 9 | 0 | 2 | 0 | 0 | 7 | 4 | 0 | 2 | 4 | 3 |
| 21A | 0 | 6 | 0 | 2 | 0 | 2 | 7 | 5 | 2 | 4 | 7 | 5 |
| 20C | 0 | 8 | 0 | 0 | 0 | 0 | 7 | 9 | 3 | 5 | 9 | 7 |
| 20A | 0 | 8 | 0 | 2 | 2 | 2 | 7 | 8 | 2 | 5 | 7 | 5 |
| 20B | 0 | 9 | 0 | 2 | 2 | 2 | 9 | 9 | 3 | 6 | 8 | 6 |
| 28 | 0 | 8 | 0 | 2 | 0 | 4 | 6 | 7 | 0 | 3 | 6 | 3 |
| 25 | 0 | 0 | 0 | 0 | 0 | 0 | 6 | 8 | 3 | 3 | 6 | 5 |
| 22 | 0 | 6 | 0 | 2 | 0 | 2 | 5 | 7 | 5 | 3 | 8 | 8 |

What is claimed is:

1. A compound of the formula 1

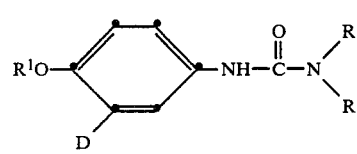

wherein D is a hydrogen atom, a halogen atom of atomic number of from 9 to 35, inclusive, or an alkyl or alkoxy group containing from 1 to 6 carbon atoms optionally substituted by one or more halogen atoms; each R independently is a hydrogen atom or an alkyl or alkoxy group containing from 1 to 4 carbon atoms or a cyclopropyl group optionally 1-substituted by an alkyl group containing from 1 to 4 carbon atoms or a halogen atom having an atomic number of from 9 to 35, inclusive; and $R^1$ is a non-aromatic oxygen-heterocyclic group having 5 to 8 atoms in a monocyclic or bicyclic ring, one of which is an oxygen atom and the remainder are carbon atoms, and containing up to 16 carbon atoms in the group.

2. A compound according to claim 1 wherein $R^1$ is a group selected from

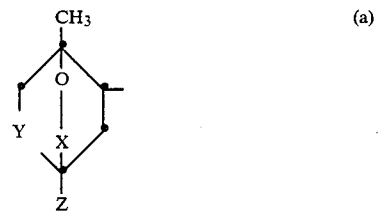

wherein X is a single bond or —CH(CH$_3$)$_2$, Y is a single bond or —CH$_2$— with the proviso that both X and Y are not a single bond; Z is H, or an optionally substituted alkyl group containing 1 to 4 carbon atoms;

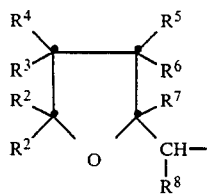

wherein each $R^2$ individually represents a hydrogen atom, a halogen atom, an optionally substituted alkyl, cycloalkyl or aryl group, each containing up to 6 carbon atoms, or two $R^2$ together represent an alkylene moiety each containing up to 6 carbon atoms, $R^3$, $R^4$, $R^5$ and $R^6$ each individually represents a hydrogen atom, a halogen atom having an atomic number of from 9 to 35, inclusive, an optionally substituted alkyl, alkoxy, alkylthio or aryl group each containing up to 6 carbon atoms or one of $R^3$ and $R^4$ and one of $R^5$ and $R^6$ together represent a carbon-carbon bond or an epoxide moiety; $R^7$ and $R^8$ each represents a hydrogen atom or optionally substituted alkyl group containing up to 6 carbon atoms;

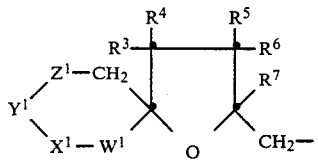

wherein $R^3$, $R^4$, $R^5$, $R^6$ and $R^7$ each individually is a hydrogen atom or an alkyl group containing from 1 to 4 carbon atoms, W is an oxygen atom or —CH$_2$—; $X^1$ is an oxygen atom or —CH$_2$—; $Y^1$ is a carbon-carbon bond, or an oxygen atom, —CH$_2$—, —C$_2$H$_4$—, or CHR$^8$— in which $R^8$ is alkoxymethyl group containing from 1 to 4 carbon atoms in the alkyl portion thereof; $Z^1$ is a carbon-carbon bond, an oxygen atom, —CH$_2$—, or —C$_2$H$_4$—; with the proviso that no two adjacent of $W^1$, $X^1$, $Y^1$ and $Z^1$ are simultaneously either oxygen atoms or —C$_2$H$_4$— and the sum of the ring atoms in $W^1$, $X^1$, $Y^1$ and $Z^1$ is an integer of from 2 to 5.

3. A compound according to claim 2 wherein $R^1$ is a group of formula (a) in which (1) X is a single bond, Y is —CH$_2$— and Z is a hydrogen atom or a 1-methylethyl group or (2) X is —C(CH$_3$)$_2$—, Y is —CH$_2$—, and Z is a hydrogen atom;

formula (b) in which each $R^2$ independently is a hydrogen atom or a methyl group or the two $R^2$'s taken together from a pentamethylene group, $R^3$, $R^4$, $R^5$, $R^6$ and $R^8$ are hydrogen atoms and $R^7$ is a hydrogen atom, a methyl or ethyl group; or formula (c) in which $W^1$ is an oxygen atom or —CH$_2$—, $X^1$ is an oxygen atom or —CH$_2$—, $Y^1$ is oxygen atom, —CH$_2$—, —C$_2$H$_4$— or CHR$^8$ in which $R^8$ is methoxymethyl, $Z^1$ is an oxygen atom or —CH$_2$—, and the sum of the ring atoms in $W^1$, $X^1$, $Y^1$ and $Z^1$ is an integer of from 3 to 5;

4. A compound according to claim 3 wherein D is chlorine, methyl or trifluoromethyl.

5. A compound according to claim 4 wherein $R^1$ is a group of formula (a) wherein X is a single bond and Z is 1-methylethyl;

formula (b) wherein each $R^2$ is a methyl group or taken together form a pentamethylene group; or formula (c) wherein (1) $W^1$ and $Z^1$ are each —CH$_2$—, $X^1$ and $Z^1$ each is an oxygen atom and $Y^1$ is —C$_2$H$_4$—.

6. A compound according to claim 5 wherein one of R is an ethyl group or a cyclopropyl group in which $R^2$ is a hydrogen atom or a methyl group.

7. A compound according to claim 6 wherein one of R is an ethyl group or a 1-methylcyclopropyl group.

8. A compound according to claim 7 wherein D is chlorine or trifluoromethyl.

9. A compound according to claim 8 wherein $R^1$ is a group of formula (a) wherein X is a single bond and Z is 1-methylethyl.

10. A compound according to claim 9 wherein D is trifluoromethyl.

11. A compound according to claim 8 wherein $R^1$ is a group of formula (b) wherein the $R^2$s taken together form a pentamethylene group and $R^7$ is an ethyl group.

12. A compound according to claim 8 wherein $R^1$ is a group of formula (c) wherein $W^1$, $Y^1$ and $Z^1$ are —CH$_2$— and $X^1$ is an oxygen atom.

13. An herbicidal composition comprising as active ingredient a herbicidally effective amount of a compound of according to claim 1 and at least one inert carrier or surface-active agent.

14. A method of controlling undesirable plant growth at a locus comprises applying to the locus or the plants a herbicidally effective amount of a compound according to claim 1.

* * * * *